United States Patent
Heiliger

(10) Patent No.: US 11,602,365 B2
(45) Date of Patent: Mar. 14, 2023

(54) CAM DRIVER FOR SURGICAL INSTRUMENTS

(71) Applicant: Covidien LP, Mansfield, MA (US)

(72) Inventor: Zachary S. Heiliger, Nederland, CO (US)

(73) Assignee: Covidien LP, Mansfield, MA (US)

( * ) Notice: Subject to any disclaimer, the term of this patent is extended or adjusted under 35 U.S.C. 154(b) by 664 days.

(21) Appl. No.: 16/747,649

(22) Filed: Jan. 21, 2020

(65) Prior Publication Data

US 2021/0220000 A1    Jul. 22, 2021

(51) Int. Cl.
*A61B 17/29* (2006.01)
*A61B 34/35* (2016.01)
(Continued)

(52) U.S. Cl.
CPC .............. *A61B 17/29* (2013.01); *A61B 34/35* (2016.02); *A61B 18/085* (2013.01); *A61B 18/1445* (2013.01); *A61B 34/71* (2016.02); *A61B 2017/2936* (2013.01); *A61B 2017/320094* (2017.08); *A61B 2018/0063* (2013.01);
(Continued)

(58) Field of Classification Search
CPC .... A61B 2017/2936; A61B 2017/2933; A61B 2017/2934; A61B 2017/2926; A61B 2017/2939; A61B 2017/294; A61B 2017/291; A61B 2017/2947; A61B 2017/2932; A61B 2017/00367; A61B 17/29; A61B 18/1445
See application file for complete search history.

(56) References Cited

U.S. PATENT DOCUMENTS

| 5,752,973 A | 5/1998 | Kieturakis |
| 5,792,135 A | 8/1998 | Madhani et al. |

(Continued)

FOREIGN PATENT DOCUMENTS

| CN | 1662174 A | 8/2005 |
| JP | H0549647 A | 3/1993 |

(Continued)

OTHER PUBLICATIONS

Extended European Search Report issued in corresponding application EP 21152622.3 dated May 19, 2021 (7 pages).

*Primary Examiner* — Majid Jamialahmadi
(74) *Attorney, Agent, or Firm* — Carter, DeLuca & Farrell LLP

(57) ABSTRACT

An end effector assembly includes first and second jaw members movable between an open and closed position to grasp tissue therebetween. First and second proximal flanges extending proximally from the second jaw member and defining a space therebetween, a proximal flange extend proximally from a proximal portion of the first jaw member and define a cam slot. A cam driver operably is coupled to the proximal flange of the first jaw member to define a space between the cam driver and the proximal flange of the first jaw member. A cam bar is disposed within the space defined between the cam driver and the proximal flange of the first jaw member. The cam bar includes a cam pin configured to move within a cam slot of the cam driver to move the first jaw member relative to the second jaw member between the open position and the closed position.

18 Claims, 12 Drawing Sheets

(51) Int. Cl.
   *A61B 34/00*   (2016.01)
   *A61B 17/32*   (2006.01)
   *A61B 18/08*   (2006.01)
   *A61B 18/14*   (2006.01)
   *A61B 18/00*   (2006.01)
   *A61B 18/18*   (2006.01)

(52) U.S. Cl.
   CPC ............... *A61B 2018/00077* (2013.01); *A61B 2018/1455* (2013.01); *A61B 2018/1807* (2013.01); *A61B 2018/1861* (2013.01)

(56) References Cited

U.S. PATENT DOCUMENTS

| | | |
|---|---|---|
| 5,848,986 A | 12/1998 | Lundquist et al. |
| 5,919,206 A | 7/1999 | Gengler et al. |
| 6,817,974 B2 | 11/2004 | Cooper et al. |
| 7,799,028 B2 | 9/2010 | Schechter et al. |
| 7,861,906 B2 | 1/2011 | Doll et al. |
| 7,918,230 B2 | 4/2011 | Whitman et al. |
| 8,439,246 B1 | 5/2013 | Knodel |
| 8,579,176 B2 | 11/2013 | Smith et al. |
| 9,055,961 B2 | 6/2015 | Manzo et al. |
| 9,474,569 B2 | 10/2016 | Manzo et al. |
| 2002/0099371 A1 | 7/2002 | Schulze et al. |
| 2002/0177842 A1 | 11/2002 | Weiss |
| 2003/0125734 A1 | 7/2003 | Mollenauer |
| 2003/0208186 A1 | 11/2003 | Moreyra |
| 2006/0022015 A1 | 2/2006 | Shelton et al. |
| 2006/0025811 A1 | 2/2006 | Shelton |
| 2007/0233052 A1 | 10/2007 | Brock |
| 2008/0015631 A1 | 1/2008 | Lee et al. |
| 2010/0274265 A1 | 10/2010 | Wingardner et al. |
| 2010/0292691 A1 | 11/2010 | Brogna |
| 2011/0118707 A1 | 5/2011 | Burbank |
| 2011/0118708 A1 | 5/2011 | Burbank et al. |
| 2011/0118709 A1 | 5/2011 | Burbank |
| 2011/0118754 A1 | 5/2011 | Dachs, II et al. |
| 2013/0079774 A1 | 3/2013 | Whitney et al. |
| 2013/0296848 A1* | 11/2013 | Allen, IV ........... A61B 18/1445 606/41 |
| 2018/0008338 A1 | 1/2018 | Kopp |

FOREIGN PATENT DOCUMENTS

| | | |
|---|---|---|
| JP | 2008546503 A | 12/2008 |
| WO | 2007002180 A2 | 1/2007 |

* cited by examiner

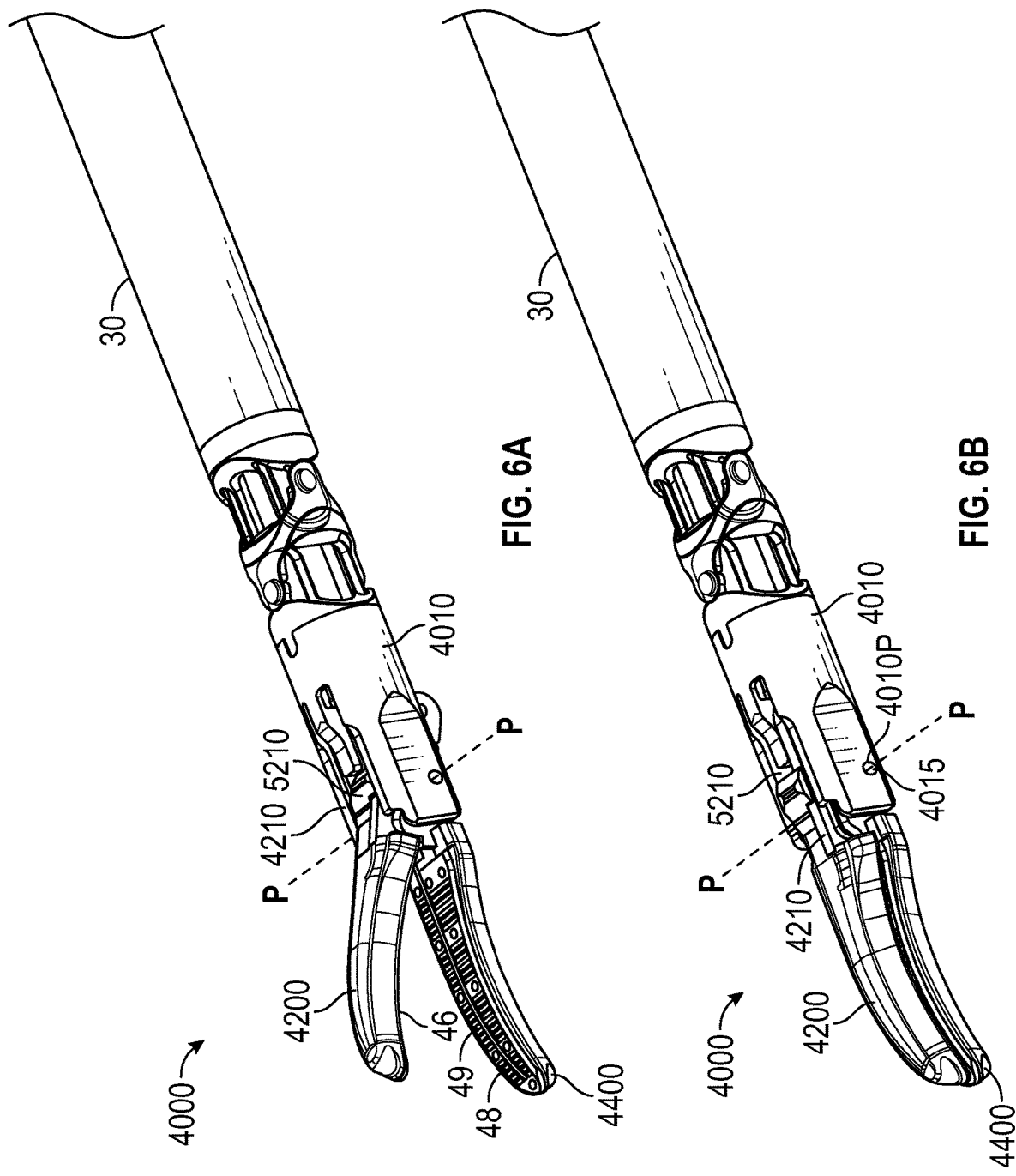

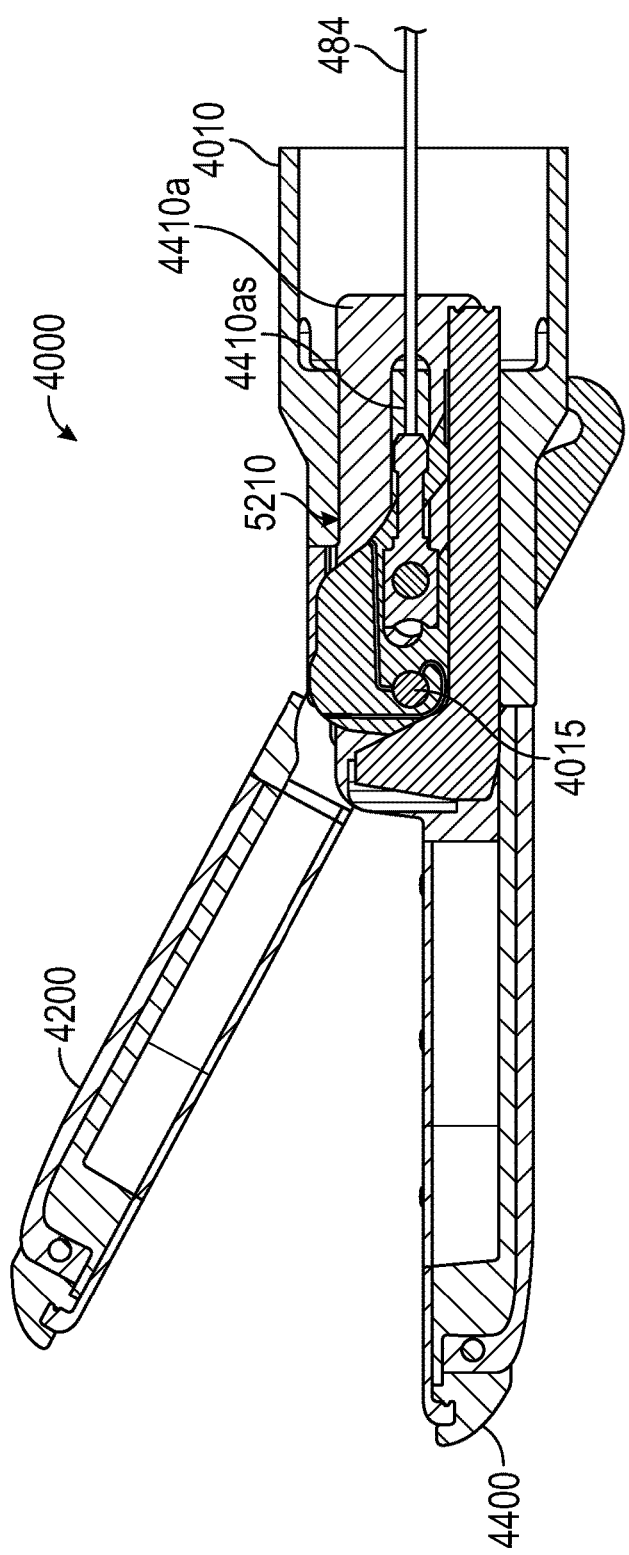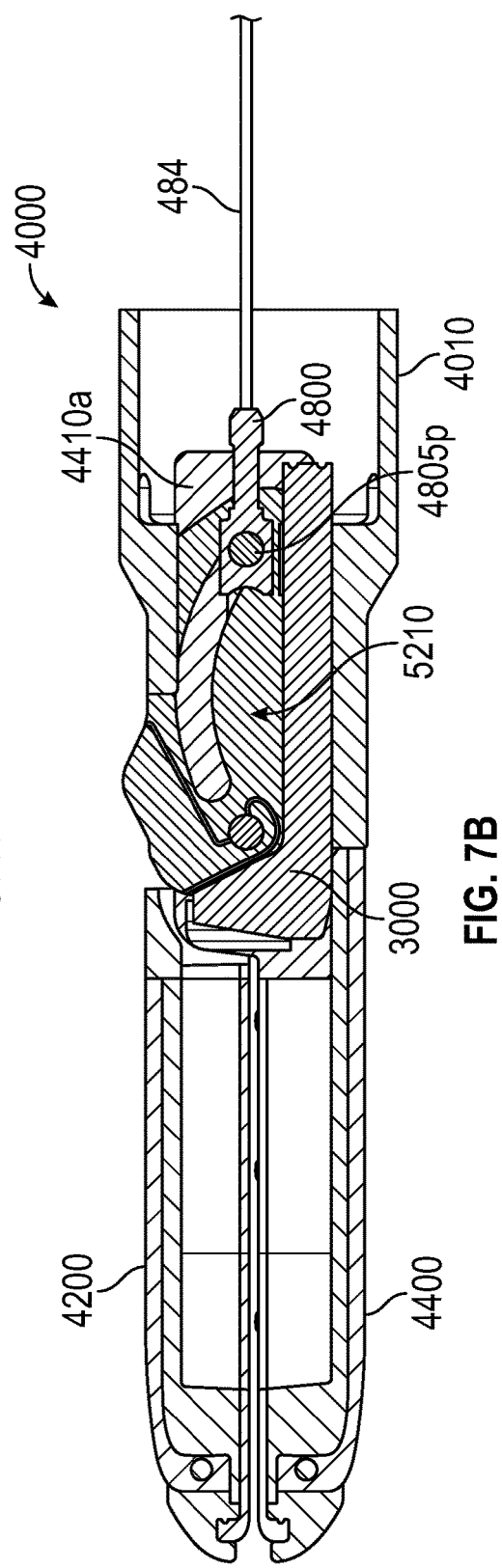
FIG. 7A
FIG. 7B

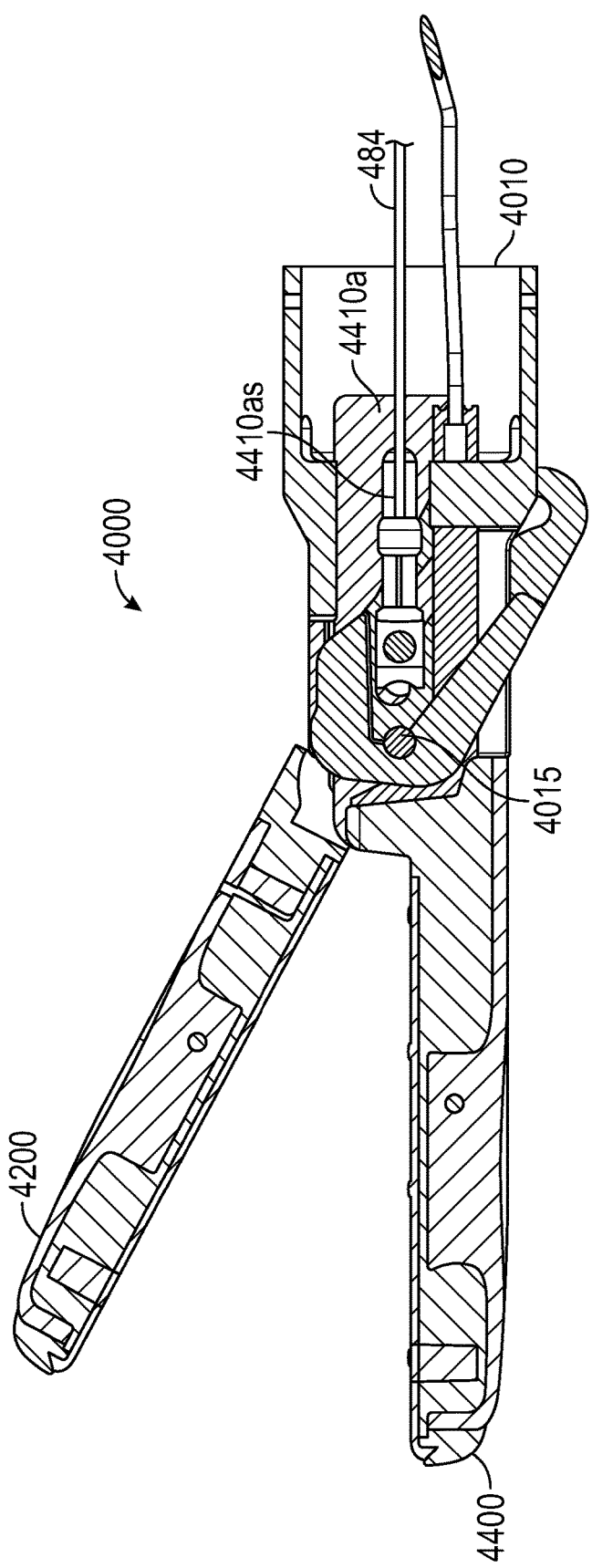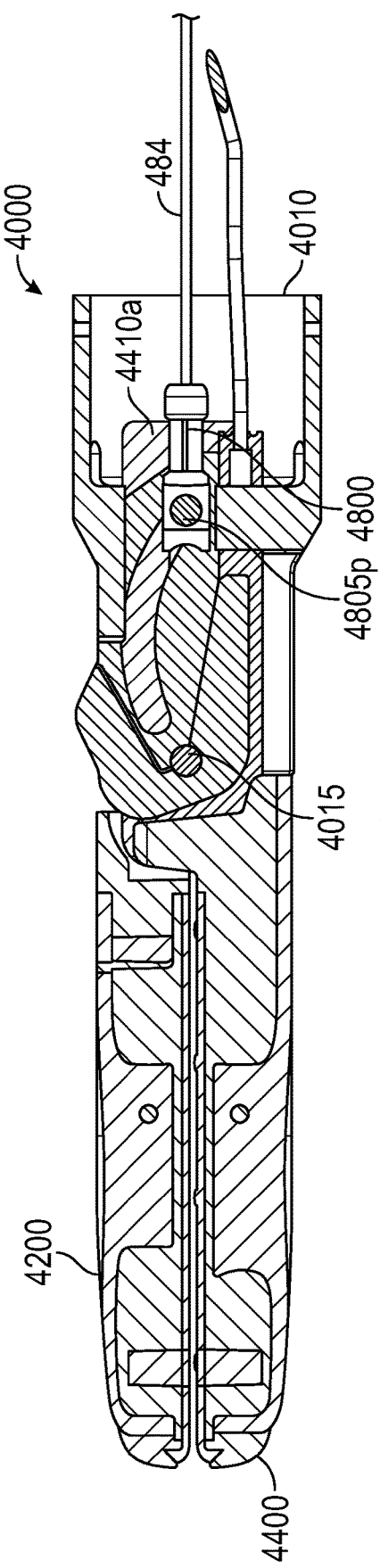
FIG. 8A
FIG. 8B

CAM DRIVER FOR SURGICAL INSTRUMENTS

FIELD

The present disclosure relates to surgical instruments and, more specifically, to drive mechanisms for surgical instruments such as, for example, for use in robotic surgical systems.

BACKGROUND

Robotic surgical systems are increasingly utilized in various different surgical procedures. Some robotic surgical systems include a console supporting a robotic arm. One or more different surgical instruments may be configured for use with the robotic surgical system and selectively mountable to the robotic arm. The robotic arm provides one or more inputs to the mounted surgical instrument to enable operation of the mounted surgical instrument.

The number, type, and configuration of inputs provided by the robotic arm of a robotic surgical system are constraints in the design of surgical instruments configured for use with the robotic surgical system. That is, in designing a surgical instrument compatible for mounting on and use with the robotic arm of a robotic surgical system, consideration should be taken in determining how to utilize the available inputs provided by the robotic arm to achieve the desired functionality of the surgical instrument.

Additionally, consideration should be taken in maintaining proper alignment of moving parts of the surgical instrument to ensure reliable and safe use thereof.

SUMMARY

As used herein, the term "distal" refers to the portion that is being described which is further from a surgeon, while the term "proximal" refers to the portion that is being described which is closer to a surgeon. The terms "about," "substantially," and the like, as utilized herein, are meant to account for manufacturing, material, environmental, use, and/or measurement tolerances and variations. Further, to the extent consistent, any of the aspects described herein may be used in conjunction with any or all of the other aspects described herein.

Provided in accordance with aspects of the present disclosure is a surgical instrument for use with a robotic surgical system. The surgical instrument includes a gearbox assembly and an end effector assembly operably coupled to the gearbox assembly. The gearbox assembly includes a drive rod and is configured to releasably couple to a robotic arm. The end effector assembly includes a first jaw member and a second jaw member movable between an open position and a closed position to grasp tissue therebetween. A first proximal flange and a second proximal flange extend proximally from the second jaw member and defining a space therebetween. A proximal flange extends proximally from a proximal portion of the first jaw member and defines a cam slot. A cam driver is operably coupled to the proximal flange of the first jaw member to define a space between the cam driver and the proximal flange of the first jaw member. A cam bar is operably coupled to the drive rod and disposed within the space defined between the cam driver and the proximal flange of the first jaw member. The cam bar includes a cam pin configured to move within a cam slot of the cam driver to move the first jaw member relative to the second jaw member between the open position and the closed position.

In an aspect, the cam driver includes a key protruding therefrom and the proximal flange includes a notch configured to receive the key of the cam driver.

In an aspect, rotation of the cam driver in a first direction about a pivot axis causes the key to apply an upward force on the notch of the proximal flange to assist in rotating the proximal flange about the pivot axis.

In an aspect, the cam driver, the proximal flange of the first jaw member, and the first proximal flange each defines a pivot opening, and the end effector assembly further includes a pivot pin disposed within those pivot openings.

In an aspect, the first jaw member is configured to pivot relative to the second jaw member about an axis defined by the pivot pin upon longitudinal translation of the cam bar.

In an aspect, the end effector assembly includes a clevis defining a pivot opening, and the pivot pin is operably coupled to the clevis via the pivot opening.

In an aspect, the cam bar includes a cam pin configured to slide along at least one of the cam slot of the cam driver or the cam slot of the proximal flange of the first jaw member.

In an aspect, the first proximal flange defines a first cam slot and the cam pin is configured to slide along the first cam slot of the first proximal flange.

In an aspect, the second proximal flange defines a second cam slot and the cam pin is configured to slide along the second cam slot of the second proximal flange.

In an aspect, the cam slot of the proximal flange and the cam slot of the cam driver are arcuate and the first cam slot of the first proximal flange and the second cam slot of the second proximal flange are straight.

Also provided in accordance with aspects of the present disclosure is an end effector assembly for use with a surgical instrument. The end effector assembly includes a first jaw member and a second jaw member movable between an open position and a closed position to grasp tissue therebetween. A first proximal flange and a second proximal flange extend proximally from the second jaw member and define a space therebetween. A proximal flange extends proximally from a proximal portion of the first jaw member and defines a cam slot. A cam driver is operably coupled to the proximal flange of the first jaw member to define a space between the cam driver and the proximal flange of the first jaw member. A cam bar is disposed within the space defined between the cam driver and the proximal flange of the first jaw member and includes a cam pin configured to slide along a cam slot of the cam driver to move the first jaw member relative to the second jaw member between the open position and the closed position.

In an aspect, the cam driver includes a key protruding therefrom and the proximal flange includes a notch configured to receive the key of the cam driver.

In an aspect, the cam driver, the proximal flange of the first jaw member, and the first proximal flange each defines a pivot opening, and the end effector assembly further includes a pivot pin disposed within those pivot openings.

In an aspect, the first jaw member is configured to pivot relative to the second jaw member about an axis defined by the pivot pin upon longitudinal translation of the cam bar.

In an aspect, the end effector assembly includes a clevis defining a pivot opening, and the pivot pin is operably coupled to the clevis via the pivot opening.

In an aspect, the cam bar includes a cam pin configured to slide along at least one of the cam slot of the cam driver or the cam slot of the proximal flange of the first jaw member.

In an aspect, the first proximal flange defines a first cam slot and the cam pin is configured to slide along the first cam slot of the first proximal flange.

In an aspect, the second proximal flange defines a second cam slot and the cam pin is configured to slide along the second cam slot of the second proximal flange.

In an aspect, the cam bar is operably coupled to a drive rod to couple the cam bar to a gearbox assembly of a surgical instrument.

In an aspect, the cam driver is fixedly coupled to the proximal flange such that rotation of the cam driver about a pivot axis drives corresponding rotation of the proximal flange about the pivot axis.

BRIEF DESCRIPTION OF THE DRAWINGS

Various aspects and features of the present disclosure are described hereinbelow with reference to the drawings wherein like numerals designate identical or corresponding elements in each of the several views.

FIG. 6A is a perspective view of the distal potion of the surgical instrument of FIG. 1 with the end effector assembly disposed in the open position;

FIG. 6B is a perspective view of the distal potion of the surgical instrument of FIG. 1 with the end effector assembly disposed in the closed position;

FIG. 7A is a side, longitudinal cross-sectional view of the end effector assembly of FIG. 1 disposed in the open position;

FIG. 7B is a side, longitudinal cross-sectional view of the end effector assembly of FIG. 1 disposed in the closed position;

FIG. 8A is a side, longitudinal cross-sectional view of the end effector assembly of FIG. 1 disposed in the open position;

FIG. 8B is a side, longitudinal cross-sectional view of the end effector assembly of FIG. 1 disposed in the closed position;

DETAILED DESCRIPTION

The described surgical instrument 10 includes an end effector assembly 4000 utilizing a cam mechanism that maintains proper alignment between the jaw members 4200, 4400 of the end effector assembly 4000 as the end effector assembly 4000 is moved between open and closed positions. In particular, the disclosed cam driver 5210 maintained proper alignment of the cam pin 4805$p$ as the end effector assembly 4000 is moved between open and closed positions by serving as a guide for the cam pin 4805$p$. The disclosed cam driver 5210 is operably coupled to a proximal flange 4210 of the first jaw member 4200 such that the cam driver 5210 provides a reaction force to the proximal flange 4210 when the cam driver 5210 is caused to pivot about a pivot axis.

Figure 1:
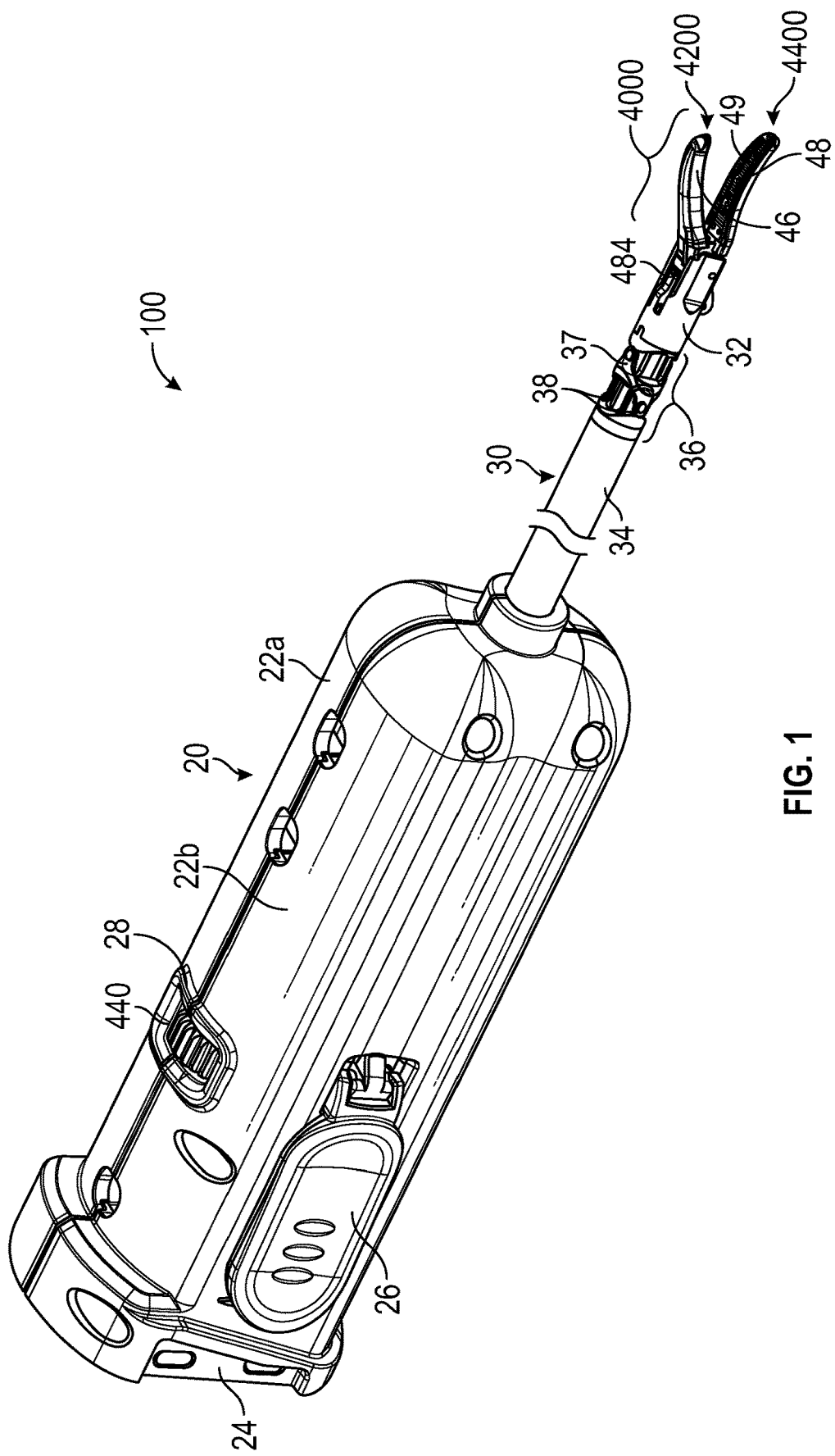
FIG. 1 is a perspective view of a surgical instrument having an end effector assembly provided in accordance with the present disclosure configured for mounting on a robotic arm of a robotic surgical system.
Figure 2A:
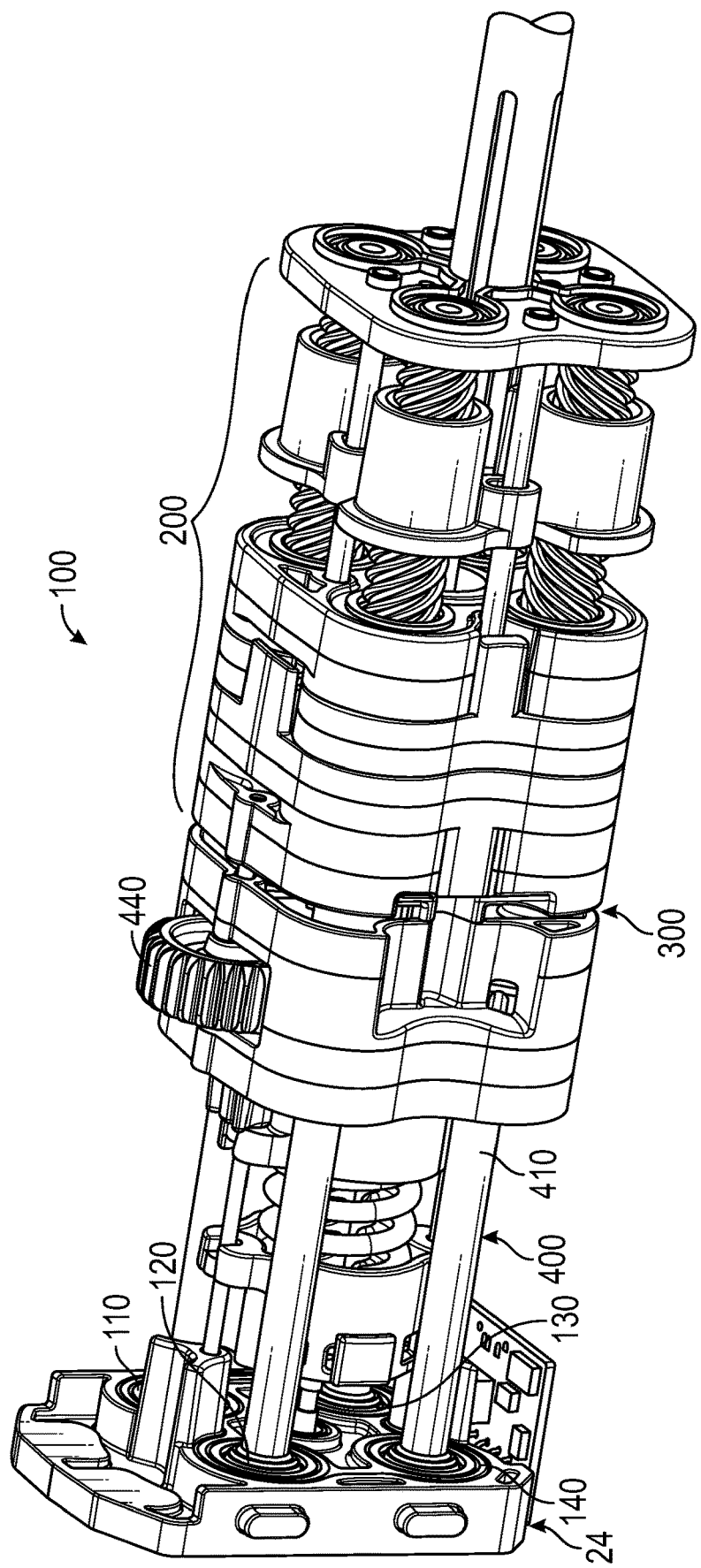
FIG. 2A is a front, perspective view of a proximal portion of the surgical instrument of FIG. 1 with an outer shell removed.
Figure 2B:
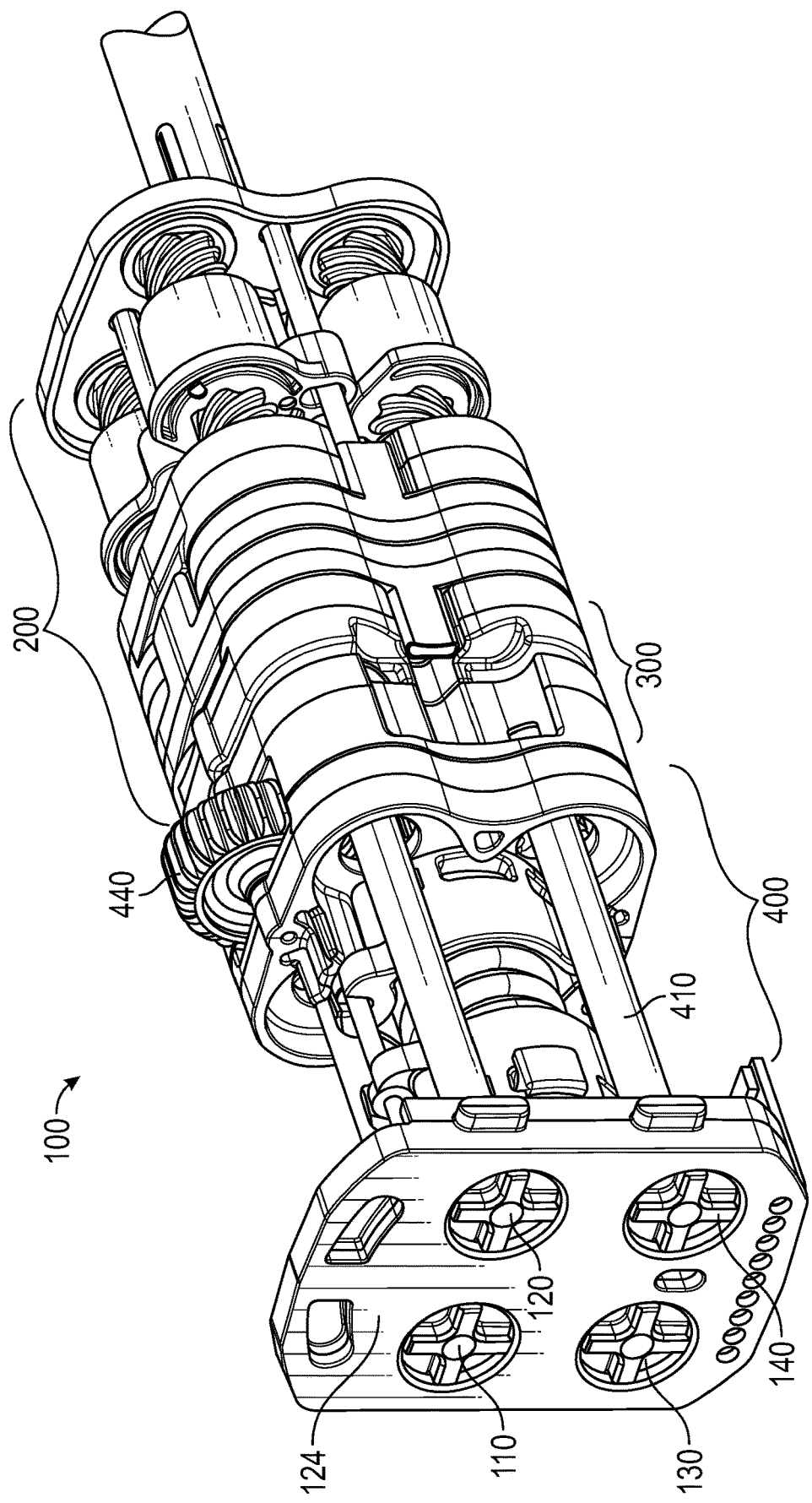
FIG. 2B is a rear, perspective view of the proximal portion of the surgical instrument of FIG. 1 with the outer shell removed.
Figure 3:
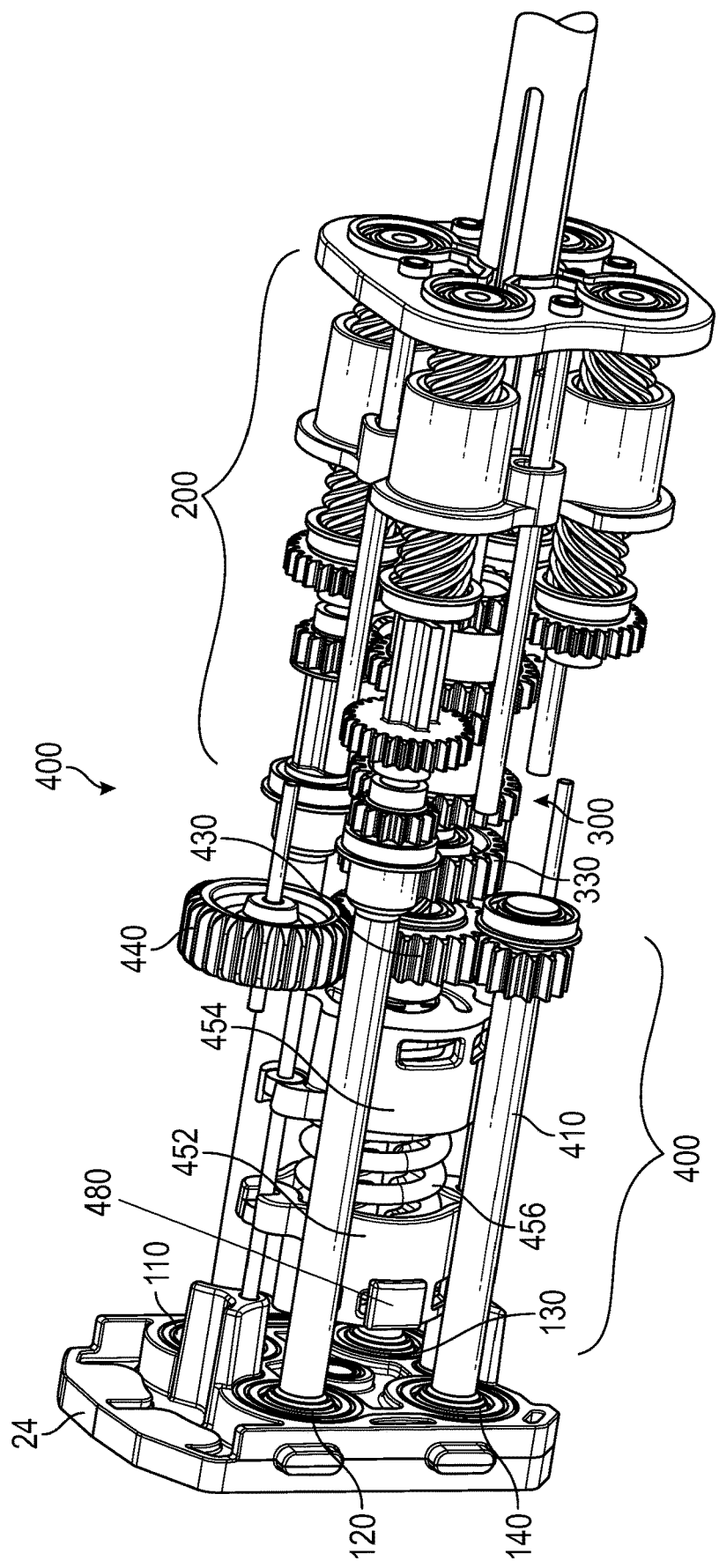
FIG. 3 is a front, perspective view of the proximal portion of the surgical instrument of FIG. 1 with the outer shell and additional internal components removed.
Figure 4:
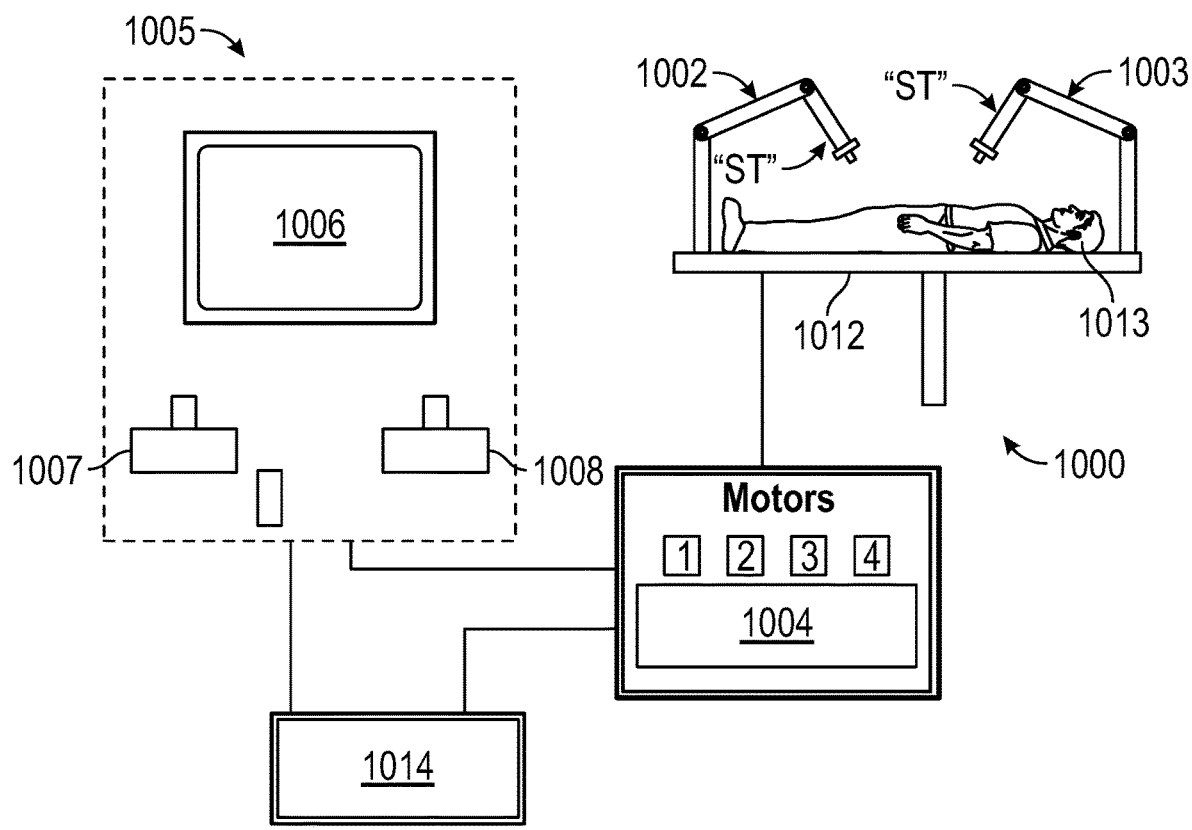
FIG. 4 is a schematic illustration of an exemplary robotic surgical system configured to releasably receive the surgical instrument of FIG. 1.
Figure 5:
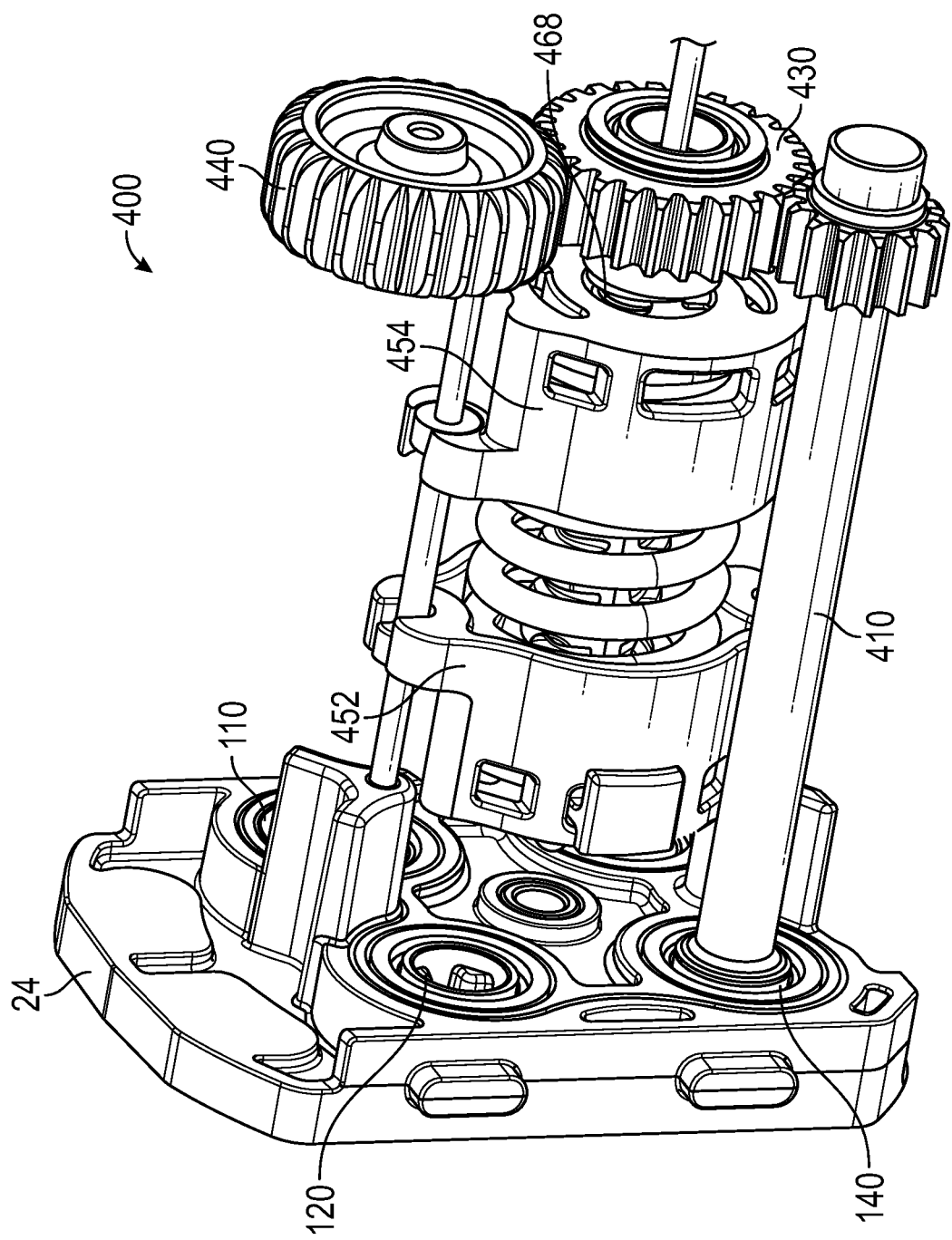
FIG. 5 is a front, perspective view of a jaw drive sub-assembly of the surgical instrument of FIG. 1.

Referring to FIGS. 1-3, a surgical instrument 10 provided in accordance with the present disclosure generally includes a housing 20, a shaft 30 extending distally from housing 20, an end effector assembly 4000 extending distally from shaft 30, and a gearbox assembly 100 (FIG. 2A) disposed within housing 20 and operably associated with end effector assembly 4000. Instrument 10 is detailed herein as an articulating electrosurgical forceps configured for use with a robotic surgical system, e.g., robotic surgical system 1000 (FIG. 4). However, the aspects and features of instrument 10 provided in accordance with the present disclosure, detailed below, are equally applicable for use with other suitable surgical instruments and/or in other suitable surgical systems.

With particular reference to FIG. 1, housing 20 of instrument 10 includes first and second body portion 22$a$, 22$b$ and a proximal face plate 24 that cooperate to enclose gearbox assembly 100 therein. Proximal face plate 24 includes apertures defined therein through which inputs 110, 120, 130, 140 of gearbox assembly 100 extend. A pair of latch levers 26 (only one of which is illustrated in FIG. 1) extending outwardly from opposing sides of housing 20 and enable releasable engagement of housing 20 with a robotic arm of a surgical system, e.g., robotic surgical system 1000 (FIG. 4). An aperture 28 defined through housing 20 permits rotation wheel 440 to extend therethrough to enable manual manipulation of rotation wheel 440 from the exterior of housing 20 to, as detailed below, permit manual opening and closing of end effector assembly 4000.

Shaft 30 of instrument 10 includes a distal segment 32, a proximal segment 34, and an articulating section 36 disposed between the distal and proximal segments 32, 34, respectively. Articulating section 36 includes one or more articulating components 37, e.g., links, joints, etc. A plurality of articulation cables 38, e.g., four (4) articulation cables, or other suitable actuators, extend through articulating section 36. More specifically, articulation cables 38 are operably coupled to distal segment 32 of shaft 30 at the distal ends thereof and extend proximally from distal segment 32 of shaft 30, through articulating section 36 of shaft 30 and proximal segment 34 of shaft 30, and into housing 20, wherein articulation cables 38 operably couple with an articulation sub-assembly 200 of gearbox assembly 100 to enable selective articulation of distal segment 32 (and, thus end effector assembly 40) relative to proximal segment 34 and housing 20, e.g., about at least two axes of articulation (yaw and pitch articulation, for example). Articulation cables 38 are arranged in a generally rectangular configuration, although other suitable configurations are also contemplated.

Continuing with reference to FIG. 1, end effector assembly 4000 includes first and second jaw members 4200, 4400, respectively. Each jaw member 4200, 4400 defines opposed tissue-contacting surfaces 46, 48, respectively. Jaw members 4200, 4400 are pivotably coupled to one another about a pivot axis "P" defined by a pivot pin 4015 and are operably coupled to one another via a cam-slot assembly, to enable pivoting of first jaw member 4200 relative to second jaw member 4400 between an open, spaced-apart, position (FIG. 6A) and a closed, approximated, position (FIG. 6B) for grasping tissue between the tissue-contacting surfaces 46, 48. As an alternative to this unilateral configuration, a bilateral configuration may be provided whereby both jaw members 4200, 4400 are pivotable relative to one another and distal segment of shaft 30.

In embodiments, longitudinally-extending knife channels 49 (only knife channel 49 of jaw member 4400 is illustrated; the knife channel of jaw member 4200 is similarly configured) are defined through tissue-contacting surfaces 46, 48, respectively, of jaw members 4200, 4400. In such embodiments, a knife assembly including a knife tube (not shown) extending from housing 20 through shaft 30 to end effector assembly 4000 and a knife blade 3000 (FIG. 7B) disposed within end effector assembly 4000 between jaw members 4200, 4400 is provided to enable cutting of tissue grasped between tissue-contacting surfaces 46, 48 of jaw members 4200, 4400, respectively. Knife tube (not shown) is operably coupled to a knife drive sub-assembly 300 of gearbox assembly 100 (FIGS. 2A-2B) at a proximal end thereof to enable selective actuation thereof to, in turn, reciprocate the knife blade 3000 between jaw members 4200, 4400 to cut tissue grasped between tissue-contacting surfaces 46, 48.

Referring still to FIG. 1, a drive rod 484 is operably coupled to cam-slot assembly of end effector assembly 4000, e.g., engaged with the cam pin thereof, such that longitudinal actuation of drive rod 484 pivots first jaw member 4200 relative to second jaw member 4400 between the spaced-apart and approximated positions. More specifically, urging drive rod 484 proximally pivots first jaw member 4200 relative to second jaw member 4400 towards the approximated position while urging drive rod 484 distally pivots first jaw member 4200 relative to second jaw member 4400 towards the spaced-apart position. However, other suitable mechanisms and/or configurations for pivoting jaw member 4200 relative to jaw member 4400 between the spaced-apart and approximated positions in response to selective actuation of drive rod 484 are also contemplated. Drive rod 484 extends proximally from end effector assembly 4000 through shaft 30 and into housing 20 wherein drive rod 484 is operably coupled with a jaw drive sub-assembly 400 of gearbox assembly 100 (FIGS. 2A-2B and 3) to enable selective actuation of end effector assembly 4000 to grasp tissue therebetween and apply a closure force within an appropriate jaw closure force range, as detailed below.

Tissue-contacting surfaces 46, 48 of jaw members 4200, 4400, respectively, are at least partially formed from an electrically conductive material and are energizable to different potentials to enable the conduction of electrical energy through tissue grasped therebetween, although tissue-contacting surfaces 46, 48 may alternatively be configured to supply any suitable energy, e.g., thermal, microwave, light, ultrasonic, ultrasound, etc., through tissue grasped therebetween for energy-based tissue treatment. Instrument 10 defines a conductive pathway (not shown) through housing 20 and shaft 30 to end effector assembly 4000 that may include lead wires, contacts, and/or electrically-conductive components to enable electrical connection of tissue-contacting surfaces 46, 48 of jaw members 4200, 4400, respectively, to an energy source (not shown), e.g., an electrosurgical generator, for supplying energy to tissue-contacting surfaces 46, 48 to treat, e.g., seal, tissue grasped between tissue-contacting surfaces 46, 48.

With additional reference to FIGS. 2A, 2B, and 3, as noted above, gearbox assembly 100 is disposed within housing 20 and includes an articulation sub-assembly 200, a knife drive sub-assembly 300, and a jaw drive sub-assembly 400. Articulation sub-assembly 200 is operably coupled between first and second inputs 110, 120, respectively, of gearbox assembly 100 and articulation cables 38 (FIG. 1) such that, upon receipt of appropriate inputs into first and/or second inputs 110, 120, articulation sub-assembly 200 manipulates cables 38 (FIG. 1) to articulate end effector assembly 4000 in a desired direction, e.g., to pitch and/or yaw end effector assembly 4000.

Knife drive sub-assembly 300 is operably coupled between third input 130 of gearbox assembly 100 and knife tube (not shown) such that, upon receipt of appropriate input into third input 130, knife drive sub-assembly 300 manipulates knife tube (not shown) to reciprocate the knife blade 3000 (FIG. 7B) between jaw members 4200, 4400 to cut tissue grasped between tissue-contacting surfaces 46, 48.

Jaw drive sub-assembly 400, as detailed below, is operably coupled between fourth input 140 of gearbox assembly 100 and drive rod 484 such that, upon receipt of appropriate input into fourth input 140, jaw drive sub-assembly 400 pivots jaw members 4200, 4400 between the spaced-apart and approximated positions to grasp tissue therebetween and apply a closure force within an appropriate closure force range.

Gearbox assembly 100 is configured to operably interface with a robotic surgical system 1000 (FIG. 4) when instrument 10 is mounted on robotic surgical system 1000 (FIG. 4), to enable robotic operation of gearbox assembly 100 to provide the above-detailed functionality. That is, robotic surgical system 1000 (FIG. 4) selectively provides inputs to inputs 110, 120, 130, 140 of gearbox assembly 100 to articulate end effector assembly 4000, grasp tissue between jaw members 4200, 4400, and/or cut tissue grasped between jaw members 4200, 4400. However, it is also contemplated that gearbox assembly 100 be configured to interface with any other suitable surgical system, e.g., a manual surgical handle, a powered surgical handle, etc. For the purposes herein, robotic surgical system 1000 (FIG. 4) is generally described.

Turning to FIG. 4, robotic surgical system 1000 is configured for use in accordance with the present disclosure. Aspects and features of robotic surgical system 1000 not germane to the understanding of the present disclosure are omitted to avoid obscuring the aspects and features of the present disclosure in unnecessary detail.

Robotic surgical system 1000 generally includes a plurality of robot arms 1002, 1003; a control device 1004; and an operating console 1005 coupled with control device 1004. Operating console 1005 may include a display device 1006, which may be set up in particular to display three-dimensional images; and manual input devices 1007, 1008, by means of which a person, e.g., a surgeon, may be able to telemanipulate robot arms 1002, 1003 in a first operating mode. Robotic surgical system 1000 may be configured for use on a patient 1013 lying on a patient table 1012 to be treated in a minimally invasive manner. Robotic surgical system 1000 may further include a database 1014, in particular coupled to control device 1004, in which are stored, for example, pre-operative data from patient 1013 and/or anatomical atlases.

Each of the robot arms 1002, 1003 may include a plurality of members, which are connected through joints, and mounted device which may be, for example, a surgical tool "ST." One or more of the surgical tools "ST" may be instrument 10 (FIG. 1), thus providing such functionality on a robotic surgical system 1000.

Robot arms 1002, 1003 may be driven by electric drives, e.g., motors, connected to control device 1004. Control device 1004, e.g., a computer, may be configured to activate the motors, in particular by means of a computer program, in such a way that robot arms 1002, 1003, and, thus, their mounted surgical tools "ST" execute a desired movement and/or function according to a corresponding input from manual input devices 1007, 1008, respectively. Control device 1004 may also be configured in such a way that it regulates the movement of robot arms 1002, 1003 and/or of the motors.

Drive rod 484, as noted above, includes a distal end portion operably coupled to cam-slot assembly of end effector assembly 4000. Drive rod 484 extends proximally through shaft 30, housing 20, and gearbox assembly 100 (see FIGS. 1-3) and a proximal end portion of drive rod 484 is engaged with proximal hub 452 of jaw drive sub-assembly 400. In an aspect, for example, a proximal end portion of drive rod 484 is engaged within lock plate 480 (FIG. 3) to secure drive rod 484 to proximal hub 452 of jaw drive sub-assembly 400. More specifically, drive rod 484 defines a waist (not shown) towards the proximal end thereof that is configured to lock in engagement within a central keyhole (not shown) of lock plate 480, e.g., via longitudinal translation of drive rod 484 into the central keyhole until the waist is aligned with the central keyhole, followed by transverse movement of drive rod 484 relative to lock plate 480, to thereby fix the proximal end portion of drive rod 484 relative to lock plate 480 and, thus, relative to proximal hub 452 due to the engagement of lock plate 482 within proximal hub 452.

Referring to FIGS. 6A and 6B, end effector assembly 4000 includes a first jaw member 4200 and a second jaw member 4400, where the first jaw member 4200 is movable relative to the second jaw member 4400 between an open position (FIG. 6A) and a closed position (FIG. 6B). The first jaw member 4200 is operably coupled to drive rod 484 (FIG. 1), via a cam driver 5210, such that longitudinal translation of the drive rod 484 causes the cam driver 5210 and the first jaw member 4200 to pivot relative to the second jaw member 4400 about a pivot axis "P".

Figure 9:
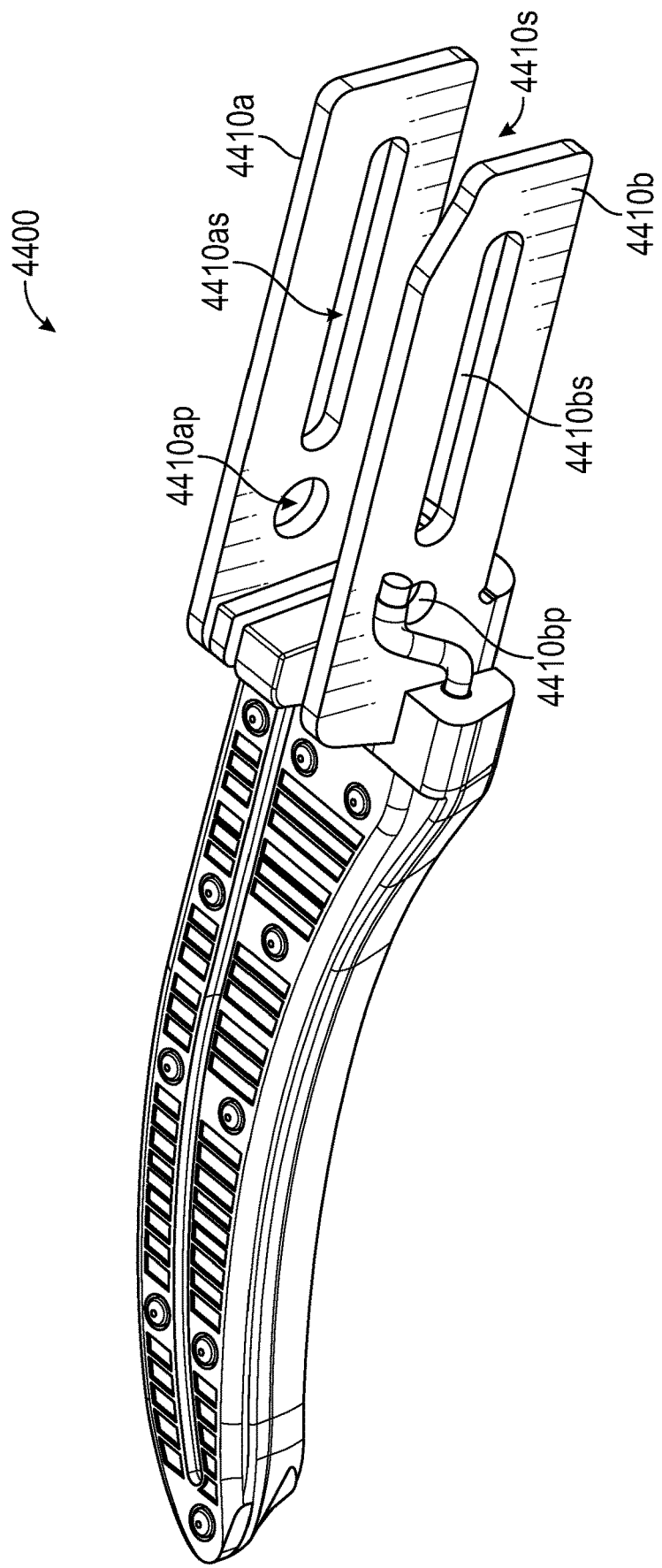
FIG. 9 is a perspective view of a jaw member of the end effector of FIG. 1.
Figure 10:
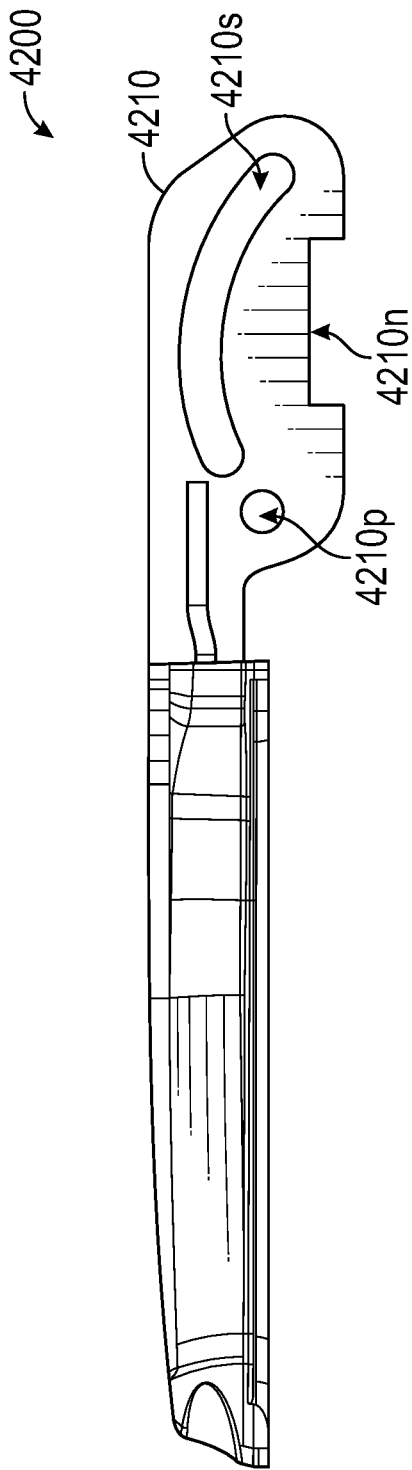
FIG. 10 is a side view of a jaw member of the end effector of FIG. 1.
Figure 11:
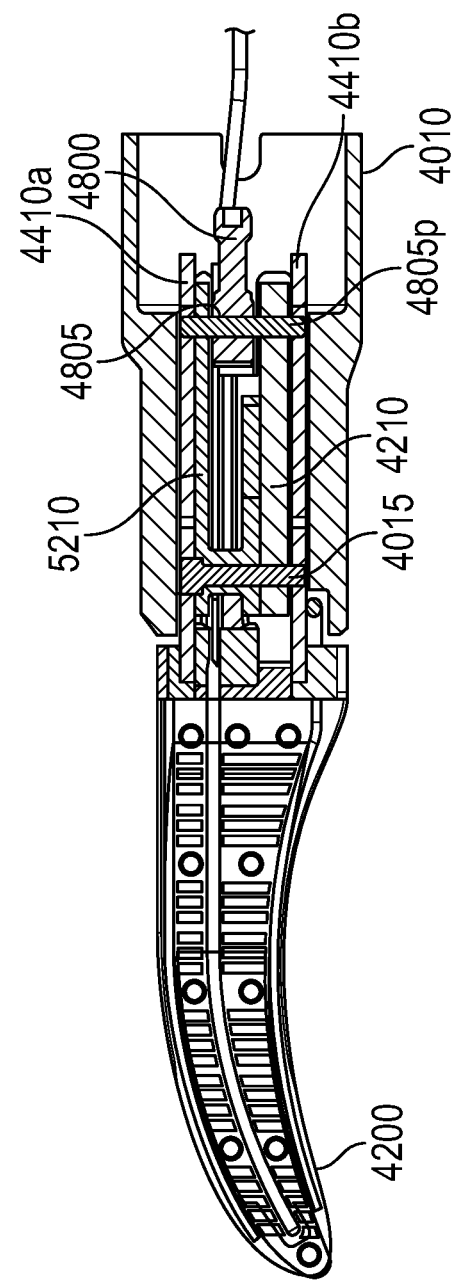
FIG. 11 is a top, cross-sectional view of the end effector assembly of FIG. 1.
Figure 12A:
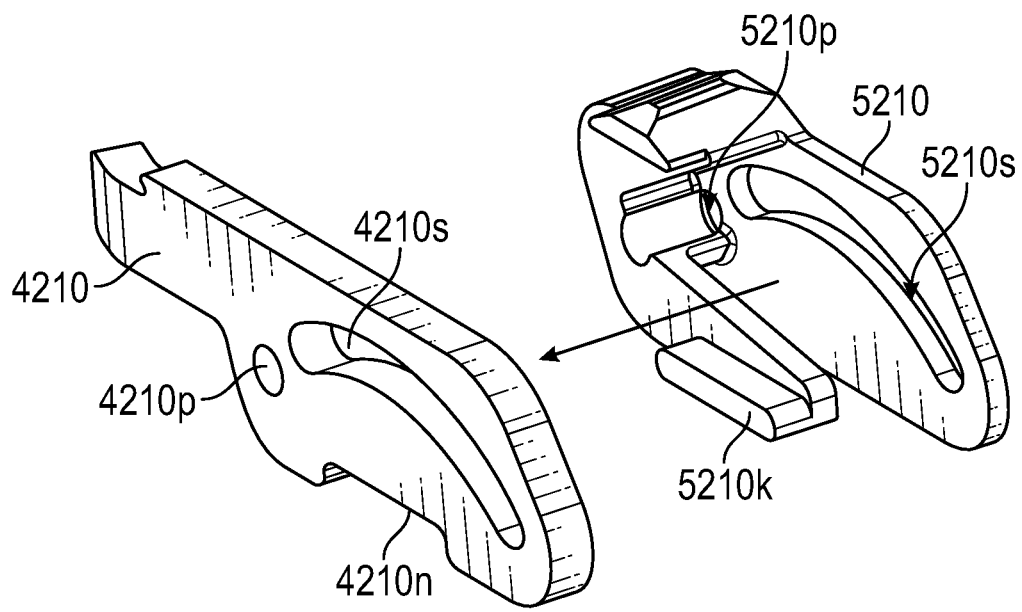
FIG. 12A is a perspective view of a cam driver separated from a proximal flange of the jaw member of FIG. 10.
Figure 12B:
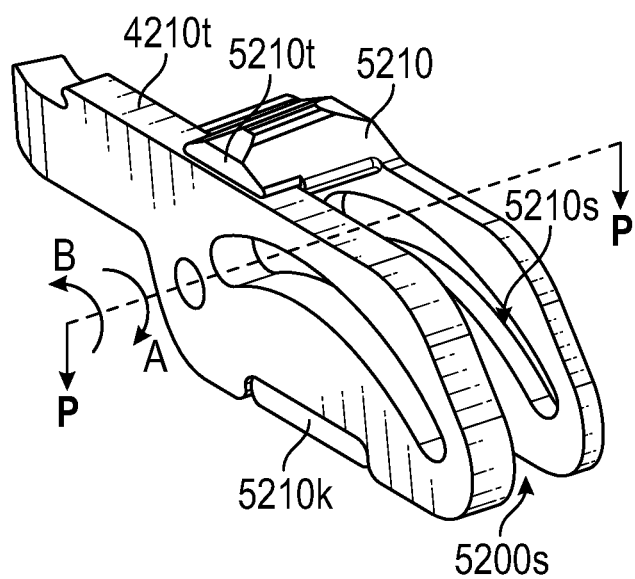
FIG. 12B is a perspective view of a cam driver coupled to a proximal flange of the jaw member of FIG. 10.

Referring to FIGS. 9-11, the first jaw member 4200 includes a proximal flange 4210 extending proximally from its proximal end. The proximal flange 4210 of the first jaw member 4200 defines a cam slot 4210s, a pivot opening 4210p, and a notch 4210n. With particular reference to FIGS. 12A and 12B, the cam driver 5210 defines a cam slot 5210s, a pivot opening 5210p, and a key 5210k. When assembled, the key 5210k of the cam driver 5210 is positioned within the notch 4210n of the proximal flange 4210, the pivot opening 5210p of the cam driver 5210 is aligned with the pivot opening 4210p of the proximal flange 4210, and the cam slot 5210s of the cam driver 5210 is aligned with the cam slot 4210s of the proximal flange 4210, while leaving a space 5200s between the cam driver 5200 and the proximal flange 4210. Additionally, a pivot pin 4010p is positioned through the pivot opening 5210p of the cam driver 5210 and the pivot opening 4210p of the proximal flange 4210 such that both components are capable of rotating about a pivot axis "P" defined by the pivot pin 4010p.

Referring to FIG. 9, the second jaw member 4400 includes a first proximal flange 4410a and a second proximal flange 4410b extending proximally therefrom and defining a space 4410s therebetween. The first proximal flange 4410a defines a longitudinal cam slot 4410as and a pivot opening 4410ap and the second proximal flange 4410b similarly defines a longitudinal cam slot 4410bs and a pivot opening 4410bp. The cam driver 5210 and the proximal flange 4210 of the first jaw member 4200 are disposed within the space 4410s defined between the first proximal flange 4410a and the second proximal flange 4410b of the second jaw member 4400, such that the pivot opening 5210p of the cam driver 5210 and the pivot opening 4210p of the proximal flange 4210 are aligned with the pivot opening 4410ap of the first proximal flange 4410a and the pivot opening 4410bp of the second proximal flange 4410b. A pivot pin 4015 defining a pivot axis "P" is disposed within the pivot opening 5210p of the cam driver 5210, the pivot opening 4210p of the proximal flange 4210, the pivot opening 4410ap of the first proximal flange 4410a, and the pivot opening 4410bp of the second proximal flange 4410b and serves to secure each of these components to a clevis 4010.

A cam bar 4800 is disposed within the space 5200c defined between the proximal flange 4210 and the cam driver 5200 and includes a cam pin 4805p configured to slide along the arcuate cam slot 5210s of the cam driver 5210, the arcuate cam slot 4210s of the proximal flange 4210 of the first jaw member 4200, and the longitudinal cam slot 4410as and the longitudinal cam slot 4410bs of the second jaw member 4400. A proximal portion of the cam bar 4800 is coupled to the drive rod 484 such that longitudinal translation of the drive rod 484 causes corresponding longitudinal translation of the cam bar 4800.

With this arrangement, distal longitudinal translation of the cam bar 4800 causes the cam driver 5210 and the proximal flange 4210 to rotate about the pivot axis "P" defined by the pivot pin 4010p to transition the end effector assembly 4000 to the open position (FIG. 7A). As described above, with this arrangement, proper alignment between the jaw members 4200, 4400 of the end effector assembly 4000 is maintained as the end effector assembly 4000 is moved between open and closed positions. Specifically, cam driver 5210 is operably coupled to proximal flange 4210 of first jaw member 4200 such that cam driver 5210 provides a reaction force to the proximal flange 4210 when the cam driver 5210 is caused to pivot about pivot axis "P".

As shown in FIG. 12B, when assembled, a tab 5210t of the cam driver 5210 engages a top surface 4210t of the proximal flange 4210 such that rotation of the cam driver 5210 about the pivot axis "P" in the direction of arrow "A" (FIG. 12B) causes the cam driver 5210 to apply a downward force on the top surface 4210t of the proximal flange 4210 in the direction of arrow "C" (FIG. 12B) to assist in rotating the proximal flange 4210 and, in turn, the first jaw member 4200 about the pivot axis "P". Additionally, proximal longitudinal translation of the cam bar 4800 causes the cam driver 5210 and the proximal flange 4210 to rotate about the pivot axis "P" in the direction of arrow "B" (FIG. 12B) to transition the end effector assembly 4000 to the closed position (FIG. 7B). The engagement of the key 5210k of the cam driver 5210 with the notch 4210n of the proximal flange 4210 enables the cam driver 5210 to apply an upward force against the proximal flange 4210 in the direction of arrow "D" (FIG. 12B) to assist in rotating the proximal flange 4210, and in turn, the first jaw member 4200 about the pivot axis "P". Although the cam driver 5210 is described and illustrated as including a key 5210k for coupling to the proximal flange 4210 of the first jaw member 4200, the cam driver 5210 or the first jaw member 4200 may include additional or alternative coupling mechanisms or structure for coupling the two components such as, for example, a pin/recess engagement, pin/hole engagement, or other alternative to provide the above-described upward/downward forces.

With additional reference back to FIGS. 1-5, in use, jaw members 4200, 4400 are initially disposed in the spaced-apart position (FIG. 6A) and, correspondingly, proximal and distal hubs 452, 454 are disposed in a distal-most position such that drive rod 484 is disposed in a distal-most position. Further, in this position, compression spring 456 is disposed in a least-compressed condition; although, even in the least-compressed condition, compression spring 456 is partially compressed due to the retention of compression spring 456 in a pre-compressed configuration between proximal and distal hubs 452, 454.

In response to an input to close end effector assembly 4000, e.g., rotational input to fourth input 140 or a manual input to rotation wheel 440, drive shaft 410 is rotated to thereby rotate input gear 420 which, in turn, rotates drive gear 430 such that distal hub 454 is translated proximally towards proximal hub 452. Proximal translation of distal hub 454 urges distal hub 454 against compression spring 456. Initially, where forces resisting approximation of jaw members 42, 44 are below a threshold corresponding to the spring value of compression spring 456, the closure force applied by jaw members 4200, 4400 is relatively low such that the urging of distal hub 454 proximally against compression spring 456 urges compression spring 456 proximally which, in turn, urges lock plate 482 and, thus, drive rod 484 proximally to pivot jaw member 4200 relative to jaw member 4400 from the spaced-apart position towards the approximated position to grasp tissue therebetween.

Upon further approximation of jaw members 4200, 4400 to grasp tissue therebetween, the forces resisting approximation of jaw members 4200, 4400, e.g., tissue resisting compression, may reach the threshold and, thus the closure force applied by jaw members 4200, 4400 may reach a corresponding threshold. In order to maintain the closure force applied by jaw members 4200, 4400 within a closure force range such as, for example, from about 3 kg/cm$^2$ to about 16 kg/cm$^2$, application of further closure force by jaw members 4200, 4400 is inhibited beyond this point despite further rotational input to fourth input 140. More specifically, once the threshold has been reached, further rotational input to fourth input 140 rotates drive shaft 410, input gear 420, and drive gear 430 to translate distal hub 454 further proximally into compression spring 456. However, rather than compression spring 456 urging proximal hub 452 further proximally to continue approximation of jaw members 4200, 4400 and increase the closure force applied therebetween, compression spring 456 is compressed, enabling proximal hub 452 and, thus, drive rod 484 to remain in position, thus inhibiting application of additional closure force between jaw members 4200, 4400.

With tissue grasped between jaw members 4200, 4400 under an appropriate closure force, energy may be supplied to jaw members 4200, 4400 to treat, e.g., seal tissue. Thereafter, the knife blade 3000 may be advanced between jaw members 4200, 4400 to cut the treated. In order to advance the knife blade 3000, a rotational input is provided to input 130 to drive rotation of input shaft 310, input gear 320, and central gear 330, thereby translating lead screw 340 distally such that a knife tube (not shown) is likewise translated distally to advance the knife blade 3000 between jaw members 4200, 4400 to cut the treated tissue. Alternatively, tissue may be cut without first treating the tissue and/or tissue may be treated without subsequent cutting.

Once tissue is cut, an opposite rotation input is provided to input 130 to return the knife blade 3000 to its initial position. Thereafter, an opposite input is provided to input 140 (or rotation wheel 440) to return jaw members 4200, 4400 back towards the spaced-apart position to release the sealed and/or cut tissue.

It will be understood that various modifications may be made to the embodiments disclosed herein. Therefore, the above description should not be construed as limiting, but merely as exemplifications of various embodiments. Those skilled in the art will envision other modifications within the scope and spirit of the claims appended thereto.

What is claimed is:

1. A surgical instrument for use with a robotic surgical system, the surgical instrument comprising:
   a gearbox assembly configured to releasably couple to a robotic arm and including a drive rod; and
   an end effector assembly operably coupled to the gearbox assembly and disposed at a distal end portion of the drive rod, the end effector assembly comprising:
      a first jaw member and a second jaw member movable between an open position and a closed position to grasp tissue therebetween;
      a first proximal flange and a second proximal flange extending proximally from the second jaw member and defining a space therebetween;
      a proximal flange extending proximally from a proximal portion of the first jaw member and defining a cam slot;
      a cam driver operably coupled to the proximal flange of the first jaw member to define a space between the cam driver and the proximal flange of the first jaw member, the cam driver defining a cam slot; and
      a cam bar operably coupled to the drive rod and disposed within the space defined between the cam driver and the proximal flange of the first jaw member, the cam bar including a cam pin configured to move within the cam slot of the cam driver to move the first jaw member relative to the second jaw member between the open position and the closed position;
      wherein the cam driver includes a key protruding therefrom and the proximal flange includes a notch configured to receive the key of the cam driver.

2. The surgical instrument of claim 1, wherein rotation of the cam driver in a first direction about a pivot axis causes the key to apply an upward force on the notch of the proximal flange to assist in rotating the proximal flange about the pivot axis.

3. The surgical instrument of claim 1, wherein:
   the cam driver defines a pivot opening;
   the proximal flange of the first jaw member defines a pivot opening; and
   the first proximal flange defines a pivot opening, and wherein the end effector assembly further includes a pivot pin disposed within the pivot opening of the cam driver, the pivot opening of the proximal flange, and the pivot opening of the first proximal flange.

4. The surgical instrument of claim 3, wherein the first jaw member is configured to pivot relative to the second jaw member about an axis defined by the pivot pin upon longitudinal translation of the cam bar.

5. The surgical instrument of claim 3, further comprising a clevis defining a pivot opening, wherein the pivot pin is operably coupled to the clevis via the pivot opening.

6. The surgical instrument of claim 1, wherein the cam pin is configured to slide along at least one of the cam slot of the cam driver or the cam slot of the proximal flange of the first jaw member.

7. The surgical instrument of claim 6, wherein the first proximal flange defines a first cam slot and the cam pin is configured to slide along the first cam slot of the first proximal flange.

8. The surgical instrument of claim 7, wherein the second proximal flange defines a second cam slot and the cam pin is configured to slide along the second cam slot of the second proximal flange.

9. The surgical instrument of claim 8, wherein the cam slot of the proximal flange and the cam slot of the cam driver are arcuate and the first cam slot of the first proximal flange and the second cam slot of the second proximal flange are straight.

10. An end effector assembly for use with a surgical instrument, the end effector assembly comprising:
- a first jaw member and a second jaw member movable between an open position and a closed position to grasp tissue therebetween;
- a first proximal flange and a second proximal flange extending proximally from the second jaw member and defining a space therebetween;
- a proximal flange extending proximally from a proximal portion of the first jaw member and defining a cam slot;
- a cam driver operably coupled to the proximal flange of the first jaw member to define a space between the cam driver and the proximal flange of the first jaw member, the cam driver defining a cam slot; and
- a cam bar disposed within the space defined between the cam driver and the proximal flange of the first jaw member and including a cam pin configured to slide along the cam slot of the cam driver to move the first jaw member relative to the second jaw member between the open position and the closed position;

wherein the cam driver includes a key protruding therefrom and the proximal flange includes a notch configured to receive the key of the cam driver.

11. The end effector assembly of claim 10, wherein:
the cam driver defines a pivot opening;
the proximal flange of the first jaw member defines a pivot opening; and
the first proximal flange defines a pivot opening, and wherein the end effector assembly further includes a pivot pin disposed within the pivot opening of the cam driver, the pivot opening of the proximal flange, and the pivot opening of the first proximal flange.

12. The end effector assembly of claim 11, wherein the first jaw member is configured to pivot relative to the second jaw member about an axis defined by the pivot pin upon longitudinal translation of the cam bar.

13. The end effector assembly of claim 11, further comprising a clevis defining a pivot opening, wherein the pivot pin is operably coupled to the clevis via the pivot opening.

14. The end effector assembly of claim 10, wherein the cam pin is configured to slide along at least one of the cam slot of the cam driver or the cam slot of the proximal flange of the first jaw member.

15. The end effector assembly of claim 14, wherein the first proximal flange defines a first cam slot and the cam pin is configured to slide along the first cam slot of the first proximal flange.

16. The end effector assembly of claim 15, wherein the second proximal flange defines a second cam slot and the cam pin is configured to slide along the second cam slot of the second proximal flange.

17. The end effector assembly of claim 10, wherein the cam bar is operably coupled to a drive rod to couple the cam bar to a gearbox assembly of the surgical instrument.

18. The end effector assembly of claim 10, wherein the cam driver is fixedly coupled to the proximal flange such that rotation of the cam driver about a pivot axis drives corresponding rotation of the proximal flange about the pivot axis.

* * * * *